US008895078B2

(12) United States Patent
Mueller

(10) Patent No.: US 8,895,078 B2
(45) Date of Patent: Nov. 25, 2014

(54) METHOD FOR PRODUCING AN EXTRACT FROM CANNABIS PLANT MATTER, CONTAINING A TETRAHYDROCANNABINOL AND A CANNABIDIOL AND CANNABIS EXTRACTS

(75) Inventor: Adam Mueller, Coburg (DE)

(73) Assignee: Bionorica Ethics GmbH, Neumarket (DE)

( * ) Notice: Subject to any disclaimer, the term of this patent is extended or adjusted under 35 U.S.C. 154(b) by 2038 days.

(21) Appl. No.: 10/399,362

(22) PCT Filed: Oct. 16, 2001

(86) PCT No.: PCT/EP01/11967
§ 371 (c)(1),
(2), (4) Date: Oct. 16, 2003

(87) PCT Pub. No.: WO02/32420
PCT Pub. Date: Apr. 25, 2002

(65) Prior Publication Data
US 2004/0049059 A1    Mar. 11, 2004

(30) Foreign Application Priority Data
Oct. 17, 2000  (DE) .................................. 100 51 427

(51) Int. Cl.
*A61K 36/00* (2006.01)
*C07D 311/80* (2006.01)
*A61K 31/35* (2006.01)

(52) U.S. Cl.
CPC .............. *C07D 311/80* (2013.01); *A61K 31/35* (2013.01)
USPC ....................................................... 424/725

(58) Field of Classification Search
None
See application file for complete search history.

(56) References Cited

U.S. PATENT DOCUMENTS

| 5,227,537 | A | 7/1993 | Stoss et al. | |
| 6,365,416 | B1 * | 4/2002 | Elsohly et al. | 436/177 |
| 6,403,126 | B1 * | 6/2002 | Webster et al. | 424/776 |

FOREIGN PATENT DOCUMENTS

| EP | 1 326 598 B1 | 7/2003 |
| JP | 55-45391 | 3/1980 |
| JP | 11-292777 | 10/1999 |

OTHER PUBLICATIONS

Awasthi, et al., "A Review on Supercritical Carbon Dioxide Extraction of Natural Products", Chemical Engineering World, 32(10): 65-71 (1997).
Nelson, Robert A., "Hemp Husbandry", Chapter 6, Cannabinoid Chemistry, (2000).
"Vascular Plants of Russia and Adjacent Countries", Humulus, (1996).
"Vascular Plants of Russia and Adjacent Countries", Cannabis L., (1996).
Veress, T., "Sample preparation by supercritical fluid extraction for quantification. A model based on the diffusion . . . ", Journal of Chromatography A, 668: 285-291 (1994).
West, David P., "Hemp and Marijuana: Myths & Realities", North American Industrial Hemp Council, Inc., (1998).
Tibor, Veress, "A szuperkritikus fluid extrakcio alkalmazasa az igazsagugyi szakertoi vizsgalatokban," Olaj, Szappan, Kozmetika, 45: 56-61 (1996).
Korte et al., "New results on hashish-specific constituents," Sieper Bulletin on Narcotics, 27: 1 35-43 (1965).

* cited by examiner

*Primary Examiner* — Chris R Tate
*Assistant Examiner* — Randall Winston
(74) *Attorney, Agent, or Firm* — Novak Druce Connolly Bove + Quigg LLP

(57) ABSTRACT

The invention relates to a method for producing an extract from *cannabis* plant matter, containing tetrahydrocannabinol, cannabidiol and optionally the carboxylic acids thereof. According to said method, the dried plant matter is ground and subjected to a $CO_2$ extraction and the primary extract obtained is separated. The invention method permits $\Delta^8$ or $\Delta^9$ tetrahydrocannabinol to be selectively obtained both from industrial hemp and from drug-producing hemp, optionally after dissolving the primary extract in ethanol, separating undesirable waxes and removing the solvent under reduced pressure.

4 Claims, 3 Drawing Sheets

METHOD FOR PRODUCING AN EXTRACT FROM CANNABIS PLANT MATTER, CONTAINING A TETRAHYDROCANNABINOL AND A CANNABIDIOL AND CANNABIS EXTRACTS

CROSS REFERENCE TO RELATED APPLICATION

This application is a national stage of PCT/EP01/11967 filed Oct. 16, 2001 and based upon DE 100 51 427.8 filed Oct. 17, 2000 under the International Convention.

BACKGROUND OF THE INVENTION

Field of the Invention

The present invention relates to a process for producing an extract containing tetra-hydrocannabinol, cannabidiol, and optionally the carboxylic acids thereof from *cannabis* plant material in accordance with the preamble of claim 1, a primary extract from *cannabis* plant material in accordance with claim 8, and a process for producing tetrahydrocannabinol in accordance with claim 13 and a process for producing cannabidiol in accordance with claim 14.

*Cannabis* (hemp), together with the genus *Humulus* (hops), belongs to the family of Cannabinaceae, with hops, for instance, not containing any cannabinoids. For the botanical and chemotaxonomical differentiation of the genus *Cannabis* there are two different concepts. One differentiates between three species, *Cannabis sativa* Linnaeus, *Cannabis indica* LAM., and *Cannabis ruderalis*, while a different theory only sees the existence of the one collective species *Cannabis sativa* L. made up of the subspecies *Cannabis sativa* ssp. *sativa* and ssp. *indica*. Moreover the *cannabis* plant is differentiated into a drug type and a fiber type, with differentiation being performed on the basis of the quantity ratio of the main cannabinoids, cannabidiol (CBD) and $\Delta^9$-tetrahydrocannabinol ($\Delta^9$-THC). Fiber hemp, whose cultivation is permitted for fiber production, must not exceed a $\Delta^9$-THC content of 0.3% relative to the dry plant mass, while the drug type may exhibit a $\Delta^9$-THC content of approx. 5%-15% relative to the dry plant mass.

The ratio of $\Delta^9$-THC to CBD in fiber hemp is mostly less than 1.5. The varieties rich in $\Delta^9$-THC may reach a ratio of 2:1 to 7:1. *Cannabis sativa* L. occurs worldwide in all warm and moderate zones with the exception of the humid tropical rain forests. It is an annual to biennial, anemogamous herb which may attain a height of up to 8 m. The dioecous, rarely monoecious inflorescences contain the active cannabinoids in the resin which is mainly secreted by the numerous glandular bracts in the leaf axils. As a general rule, all the plant parts of *Cannabis sativa* L. with the exception of the seeds may contain cannabinoids. The highest cannabinoid concentrations are found in the floral bracts and fruit stalks. The leaves have a low content of cannabinoids as a function of leaf age, while the stalk and particularly the root exhibit clearly lower cannabinoid contents.

In Germany, the known *cannabis* preparations having a hallucinogenic effect, marijuana and hashish, are subject to the regulations of the Narcotics Act as non-trafficable narcotics like opium, morphine, heroin, cocaine and LSD.

*Cannabis sativa* L. contains more than 420 different components, with 61 compounds of these belonging to the class of cannabinoids. These are lipophilic, nitrogen-free, mostly phenolic compounds. The neutral cannabinoids are biogenetically derived from a monoterpene and a phenol, the acidic cannabinoids from a monoterpene and a phenolic acid, and present a $C_{21}$ parent substance. In literature, two different numbering systems for cannabinoids are found. The older numbering system is based on the monoterpene skeleton, whereas the more recent IUPAC designation which is exclusively employed in the present application, relates to the dibenzopyrane skeleton.

Among the most important cannabinoids there are:
$\Delta^9$-tetrahydrocannabinol $\Delta^9$-THC
$\Delta^8$-tetrahydrocannabinol $\Delta^8$-THC
cannabichromene CBC
cannabidiol CBD
cannabigerol CBG
cannabinidiol CBND
cannabinol CBN Besides the above mentioned cannabinoids, the associated carboxylic acids thereof are moreover found in the raw drug as well as in the plant products. As a general rule, the carboxylic acids have the function of a biosynthetic precursor. Thus, for instance, the tetrahydrocannabinols $\Delta^9$- and $\Delta^8$-THC and CBD are generated in vivo from the THC carboxylic acids by decarboxylation from the associated cannabidiol carboxylic acids.

$\Delta^8$-THC may, for instance, also form upon cyclization of CBD. Another possibility is that $\Delta^8$-THC may be generated under certain conditions, for instance acidity, by double bond isomerism from $\Delta^9$-THC or its carboxylic acid, respectively.

In the following, the chemical structures of some cannabinoid active principles and the nomenclature of the two active principles of tetrahydrocannabinol are specified, which bear the IUPAC names (6aR-trans)-6a,7,8,10a-tetrahydro-6,6,9-trimethyl-3-pentyl-6H-dibenzo[b,d]pyran-1-ol or $\Delta^9$-THC, and (6aR-trans)-6a,7,10,10a-tetrahydro-6,6,9-trimethyl-3-pentyl-6H-dibenzo[b,d]pyran-1-ol or $\Delta^8$-THC. $\Delta^9$-THC is also known under the designation of Dronabinol.

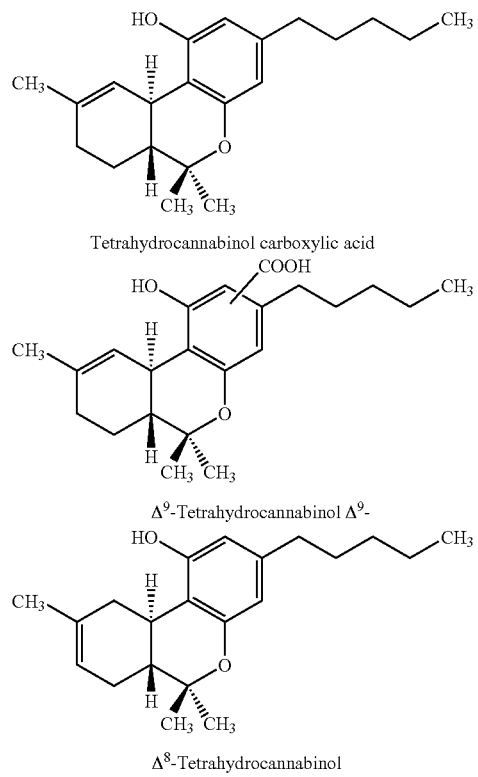

Tetrahydrocannabinol carboxylic acid $\Delta^9$-Tetrahydrocannabinol $\Delta^9$-

$\Delta^8$-Tetrahydrocannabinol

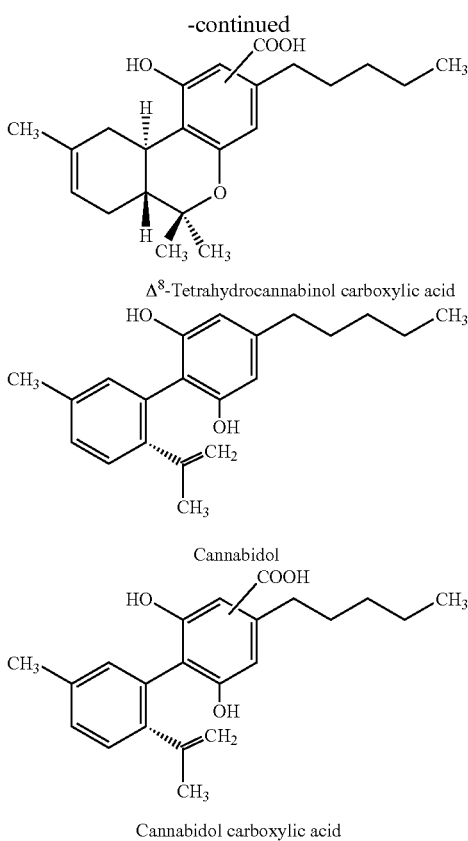

Δ⁸-Tetrahydrocannabinol carboxylic acid

Cannabidol

Cannabidol carboxylic acid

In the framework of the present invention, the expression "tetrahydrocannabinol" or "THC"—where not otherwise specified—is to encompass any isomers, in particular double bond isomers.

In many cultures and for a long time, *cannabis* has been a traditional drug and a remedy. Up into the 20th century, *cannabis* was employed for the most variegated ailments—from asthma to migraine. Restrictive legislation against *cannabis* on the part of the USA, however, brought about its complete disappearance from the pharmacopoeia and from physicians' repertories of treatment.

In the meantime, many of the therapeutical effects handed down are coming to be confirmed in clinical research. At present, the pharmacological use of *cannabis* active principles is of importance essentially in the following indications:

the appetite stimulating effect, in particular in the case of AIDS-related afflictions accompanied by cachexia and wasting syndrome, the antiemetic action for inhibiting nausea and vomiting, particularly in connection with chemotherapy under administration of cytostatic agents, the reduction of muscle cramps and spasms in multiple sclerosis and traverse lesions of the cord with paraplegia, pain and migraine treatment—in chronic pain therapy also complementarily with opioid treatment, lowering intra-ocular pressure in glaucoma, mood improvement, and in particular cannabidiol as an anti-epileptic.

Owing to the interesting therapeutic range of the cannabinoids, a number of experiments were carried out to enrich, isolate and/or synthesize the cannabinoids exclusively from drug hemp.

Thus, e.g., DE 41 00 441 A1 discloses a process for producing 6,12-dihydro-6-hydroxy-cannabidiol and its use for producing trans-Δ⁹-tetrahydrocannabinol. In particular DE 41 00 441 A1 describes the manufacture of 6,12-dihydro-6-hydroxy-cannabidiol, which is obtained by reacting olivetol and cis-p-menth-2-ene-1,8-diol, and its further reaction to trans-Δ⁹-tetrahydrocannabinol by using suitable catalysts.

A drawback of this prior-art process, however, is the relatively high expenditure and the ultimately costly product obtained.

Apart from this, solvent extraction, e.g. with the aid of ethanol, and steam distillation of *cannabis* constituents is known; in particular a hashish oil (*cannabis* resin extract) also referred to as Oil, Red Oil or Indian Oil is known, which is produced with the aid of solvent extraction or distillation from *cannabis* herb or *cannabis* resin and which is a dark brown, viscous and sticky oil. The oil thus obtained is subsequently mostly diluted with edible oil for improved handling and contains up to 65% of the hallucinogenic agent Δ⁹-THC (Kleiber/Kovar: *Auswirkungen des Cannabiskonsums: Eine Expertise zu pharmakologischen and psychosozialen Konsequenzen*, Stuttgart: Wiss. Verl.-Ges. 1998).

Dronabinol, Δ⁹-THC, has meanwhile been approved in the USA in accordance with USP [United States Pharmacopeia] 24, pp. 613, 614 as a medicament—also in capsule form—. In accordance with this monography, dronabinol contains no less than 95% of Δ⁹-THC and no more than 2% of Δ⁸-THC.

As of Feb. 1, 1998, dronabinol may be prescribed as an anaesthetic in Germany.

WO 00/25127 A1 moreover relates to the extraction of hemp for the isolation of tetrahydrocannabinol from the natural *cannabis* plant. What is described in particular is an extraction process with an apolar organic solvent, followed by fractional distillation under reduced pressure in order to produce distillates having high tetrahydrocannabinol contents. As suitable apolar solvents, lower alkanes such as, e.g., hexane, heptane or isooctane are named in WO 00/25127 A1.

In accordance with Examples 1, 2, 3, 4 and 7 of reference WO 00/25127 A1, exclusively drug hemp having tetrahydrocannabinol dry concentrations of 2.20%-7.82% is extracted with hexane.

Such primary hexane extracts in accordance with WO 00/25127 A1 contain 28.76% (Example 2) up to a maximum of 41.2% (Example 3) of tetrahydrocannabinol.

Apart from tetrahydrocannabinol, WO 00/25127 A1 does not disclose any further constituents of the hexane primary extract.

Starting out from the above explained prior art and from the new legal situation in the Federal Republic of Germany, it accordingly was the object of the present invention to provide Δ⁹-tetrahydrocannabinol, Δ⁸-tetrahydro-cannabinol and cannabidiol in pure form and as an extract in the form of preparations for medical applications, wherein the active principles should preferably be obtained from hemp varieties having low cannabinoid contents for the reason of better availability.

In terms of process technology, this object is accomplished through the characterizing features of claims 1, 13 and 14. With regard to an extract having the main constituents Δ⁹-THC, Δ⁸-THC and CBD, the above object is accomplished through the characterizing features of claim 8.

In accordance with the invention, a primary extract containing tetrahydrocannabinol, cannabidiol, and optionally the carboxylic acids thereof, is obtained from *cannabis* plant material in that the dried plant material is comminuted, the plant material is extracted with the aid of CO₂ under supercritical pressure and temperature conditions at a temperature in the range of approx. 31° C. to 80° C. and at a pressure in the range of approx. 75 bar to 500 bar, or in the subcricital range at a temperature of approx. 20° C. to 30° C. and a supercritical pressure of approx. 100 bar to 350 bar; or extracted under subcricital pressure and temperature conditions; and the obtained primary extract is separated under subcricital conditions, or under conditions that are subcricital in terms of pressure and supercritical in terms of temperature.

In terms of cannabinoids, the primary extract of the invention contains high proportions of cannabidiol carboxylic acid (CBDS), cannabidiol (CBD), and $\Delta^9$-tetra-hydrocannabinol carboxylic acid ($\Delta^9$-THCS), and $\Delta^9$-THC (when drug hemp is used).

The production of $CO_2$ extracts is known in principle. Thus, e.g., DE 198 00 330 A1 discloses the production of a pharmaceutically active extract from *Tanacetum parthenium* through $CO_2$ extraction with the aid of an extraction plant as used in the present invention.

As a particularly preferred *cannabis* plant material, for reasons of procurement on an industrial scale, one from *Cannabis sativa* L., in particular hemp of the fiber type, i.e. so-called industrial hemp, is used.

Owing to currently valid legislation, industrial hemp species of the fiber type may contain 0.3% of $\Delta^9$-THC at maximum in the Federal Republic of Germany; for Switzerland an upper limit of 0.5% $\Delta^9$-THC applies, based on the dry plant mass in either case.

The like industrial hemp varieties may be cultivated both in the Federal Republic of Germany and in Switzerland, for example, while requiring neither any complicated cultivating permission nor any complicated safety installations during storage.

It is thus advantageous if *cannabis* plant material of the fiber type may be used for the production of primary extracts containing $\Delta^9$-THC and CBD, for it is possible to employ such starting material having a low $\Delta^9$-THC content for the inventive process without any further operating and handling permissions as are required in the case of drug hemp types.

Varieties entering into consideration here are in particular the French varieties Fedora 19, Felina 45 and Futura 77, the Hungarian varieties Kompolti and Uniko-B and the Finnish variety Finola 314, for the average for all varieties lies clearly below the specified limits (Mediavilla, V. and Brenneisen, R. 1996: Mitt. Ges. Pflanzenbauwiss. 9: 243-244).

When it is possible to employ drug hemp types, however, the $\Delta^9$-THC content in the primary extract is higher than in one produced of fiber hemp.

The addition to the $CO_2$ of an entraining agent selected from the group consisting of: propane, butane, ethanol and water, has the advantage that hereby the yields for $\Delta^9$-THC and CBD may be increased without involving the drawbacks as with an extract produced, e.g., with ethanol or ethanol/water or methanol/chloroform or with other chlorinated hydrocarbons.

Typically the entraining agent concentrations are in the range of 1-10% based on the employed quantity of $CO_2$.

The extraction process of the invention preferably operates in the supercritical range at a temperature of approx. 31° C. to 80° C. and a pressure of approx. 75 bar to 500 bar, in particular at a temperature of approx. 45° C. to 65° C. and a pressure of approx. 100 bar to 350 bar, preferably at a temperature of approx. 60° C. and a pressure of approx. 250 bar.

In the subcricital range, in contrast, a temperature of approx. 20° C. to 30° C. and a supercritical pressure of approx. 100 bar to 350 bar are used.

The measure of arranging a layer of adsorbent on the material to be extracted downstream relative to the $CO_2$ flow has the advantage that monoterpenes and sesquiterpenes as well as alkaloids, flavonoids and chlorophylls may be separated out, so that the inventive primary extracts are even the more superior to the ethanol extracts known in the prior art and to the extracts prepared with the aid of chlorinated hydrocarbons, for the latter in any case are fairly high in mono- and sesquiterpenes as well as chlorophylls, flavonoids and alkaloids.

As an alternative, the $CO_2$ laden with THC and CBD as well as with proportions of reduced mono- and sesquiterpenes, flavonoids, chlorophylls and alkaloids may also be passed over adsorbers charged with adsorbents or separators (FIG. 1).

Preferred adsorbents are those selected from the group comprised of: silica gel, diatomaceous earth, bentonites, bleaching earth, activated carbons, in particular magnesium oxide and alumina, as well as mixtures thereof.

In order to increase the extraction yield, it is preferred to repeat extraction at least once, with extraction preferably being repeated with diatomaceous earth and/or some other adsorbent.

The inventive primary extracts from *Cannabis* plant material containing $\Delta^9$-THC and cannabidiol are substantially free from monoterpenes and sesquiterpenes and moreover free from alkaloids and flavonoids, and contain practically no chlorophylls.

Where a hemp of the drug type is used as a starting material, $\Delta^9$-THC is the main constituent of the primary extract, and CBD the second highest proportion.

Where, however, a hemp of the fiber type is used as a starting material, which is being preferred, CBD and in a given case the carboxylic acids thereof are found as the main constituents of the primary extract.

The primary extract of the invention contains at least reduced proportions of monoterpene and sesquiterpene hydrocarbons, alkaloids, flavonoids and chlorophylls, and is preferably already free from these components, in particular from alkaloids, flavonoids and chlorophylls.

Where undesirable waxes are present in certain industrial and drug hemp varieties, these are purified after completed primary extraction and decarboxylation by subsequent dissolution of the primary extract, e.g. in cold (20° C.) ethanol or ethanol solution, and separated from the non-dissolved wax by filtration. The filtration residue amounts to approximately 3-5%. In order to obtain the purified extract, the solvent, e.g. ethanol, is again removed under reduced pressure.

In order to obtain $\Delta^9$-THC and CBD from the primary extract thus purified, the cannabidiol carboxylic acids und $\Delta^9$-tetrahydrocannabinol carboxylic acids contained in the primary extract are decarboxylated into cannabidiol and $\Delta^9$-tetrahydrocannabinol through increase in temperature.

Where $\Delta^9$-THC is to be obtained as the main constituent or in pure form, the CBD may be reacted into $\Delta^9$-THC through catalyzed cyclization.

Here a $\Delta^8$-THC may form depending on process conditions, which in itself also possesses interesting pharmacological properties. Thus $\Delta^8$-THC may, for example, be employed as an antiemetic in pediatric oncology.

Where the primary extract was obtained from fiber hemp and the entire CBD is to be transformed to $\Delta^8$-THC and $\Delta^9$-THC, cyclization into $\Delta^8$-THC and $\Delta^9$-THC takes place during preparation of the secondary extract. Cyclization takes place under the following conditions:

The decarboxylated primary extract is mixed with a water-binding agent and a catalyst defined more closely hereinbelow. The mixture is treated in a high-pressure extraction plant (FIG. 2) with supercritical $CO_2$, preferably at 300 bar and 70°

C. By this treatment, the CBD present in the primary extract is substantially reacted to $\Delta^8$-THC and $\Delta^9$-THC.

The obtained extract is separated out under pressure and temperature conditions subcricital for $CO_2$, preferably at approx. 55 bar and approx. 25° C.

As a water-binding agent zeolitic molecular sieves having a pore size of 3-10 Å, preferably 5 Å may be used, and useful catalysts are metal-containing halogen salts containing the metals tin, zinc, iron or titanium, preferably zinc chloride.

The secondary extract thus obtained only contains very little CBD and is highly enriched in $\Delta^8$-THC and $\Delta^9$-THC.

Suitably for obtaining pure or nearly pure $\Delta^9$-THC or $\Delta^8$-THC, respectively, a treatment in a high-pressure apparatus with supercritical $CO_2$ is performed as described in the following (FIG. 3).

To this end, preferably a high-pressure column (FIG. 3) subdivided into segments, comprising a bottom segment for dissolving the primary extract in supercritical $CO_2$, a purification segment filled, e.g., with silica gel (mean particle size of 0.02 mm to 0.2 mm, preferably 0.1 mm), a head segment for discharging the mixture dissolved in supercritical $CO_2$ of CBD, $\Delta^8$-THC and $\Delta^9$-THC into three separating vessels for separate separation of the purified CBD and the purified $\Delta^8$-THC and $\Delta^9$-THC.

The extraction conditions prevailing for purification in the column are supercritical for $CO_2$, preferably 180 bar and 55° C., in the first separating vessel where CBD is separated out for $CO_2$ subcricital conditions in terms of pressure and supercritical conditions in terms of temperature, preferably 70 bar and 50° C. In the second and third separating vessels, where $\Delta^8$-THC and $\Delta^9$-THC are separated out, conditions subcricital for $CO_2$ in terms of pressure and temperature are to prevail, in the second separating vessel preferably 60 bar and 30° C., in the third separating vessel preferably 55 bar and 25° C.

If fiber hemp is used, it may possibly be necessary to further purify the tetrahydrocannabinol products $\Delta^8$-THC and $\Delta^9$-THC thus obtained with the aid of additional processes such as preparative chromatography or HPLC.

Where the primary extract was obtained from drug hemp and purified CBD is furthermore desired as an end product besides purified $\Delta^9$-THC, the cyclization of CBD into $\Delta^8$-THC and $\Delta^9$-THC, or the production of a secondary extract is omitted. $\Delta^8$-THC is an isomer of $\Delta^9$-THC and forms substantially during the cyclization of CBD zu $\Delta^9$-THC as well as in the presence of acids. Under certain circumstances it is necessary for the $\Delta^8$-THC, $\Delta^9$-THC and CBD thus obtained to be purified by further processes such as preparative chromatography or HPLC.

The reaction scheme of these reactions is given below:

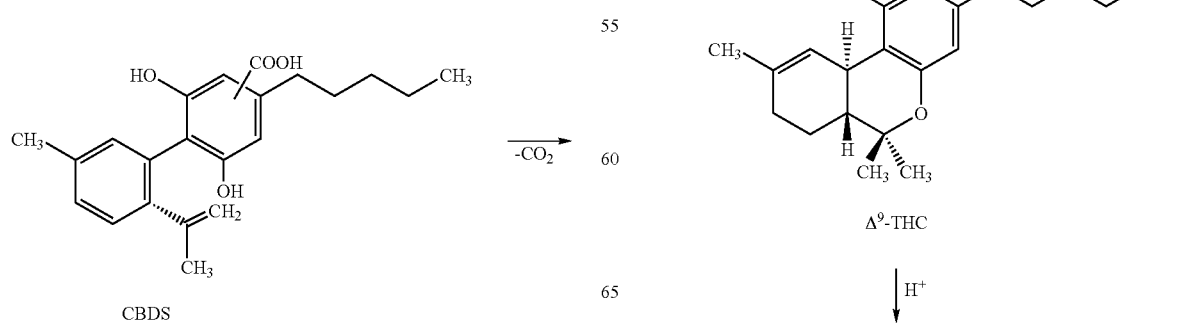

-continued

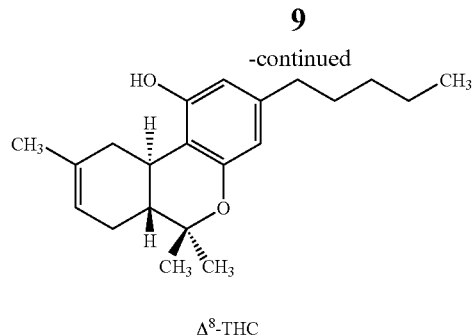

$\Delta^8$-THC

As may be seen from the scheme of formulae, $\Delta^9$-THC may under the action of acids isomerize to $\Delta^8$-THC.

As cannabidiol taken for itself has interesting pharmacological properties while furthermore lacking the psychotropic hallucinogenic effect of $\Delta^9$-THC, cannabidiol itself is also of interest for practical application because it may be used, e.g., as an anti-epileptic.

Cannabidiol may be obtained in accordance with the inventive process of claim 15.

$\Delta^8$-THC by itself also has substantially lower psychotropic hallucinogenic effects than $\Delta^9$-THC and may be obtained in accordance with claim 14.

BRIEF DESCRIPTION OF THE DRAWINGS

Further advantages and features of the present invention result from the description of practical examples and from the drawings, wherein.

DETAILED DESCRIPTION OF THE INVENTION

Figure 1:
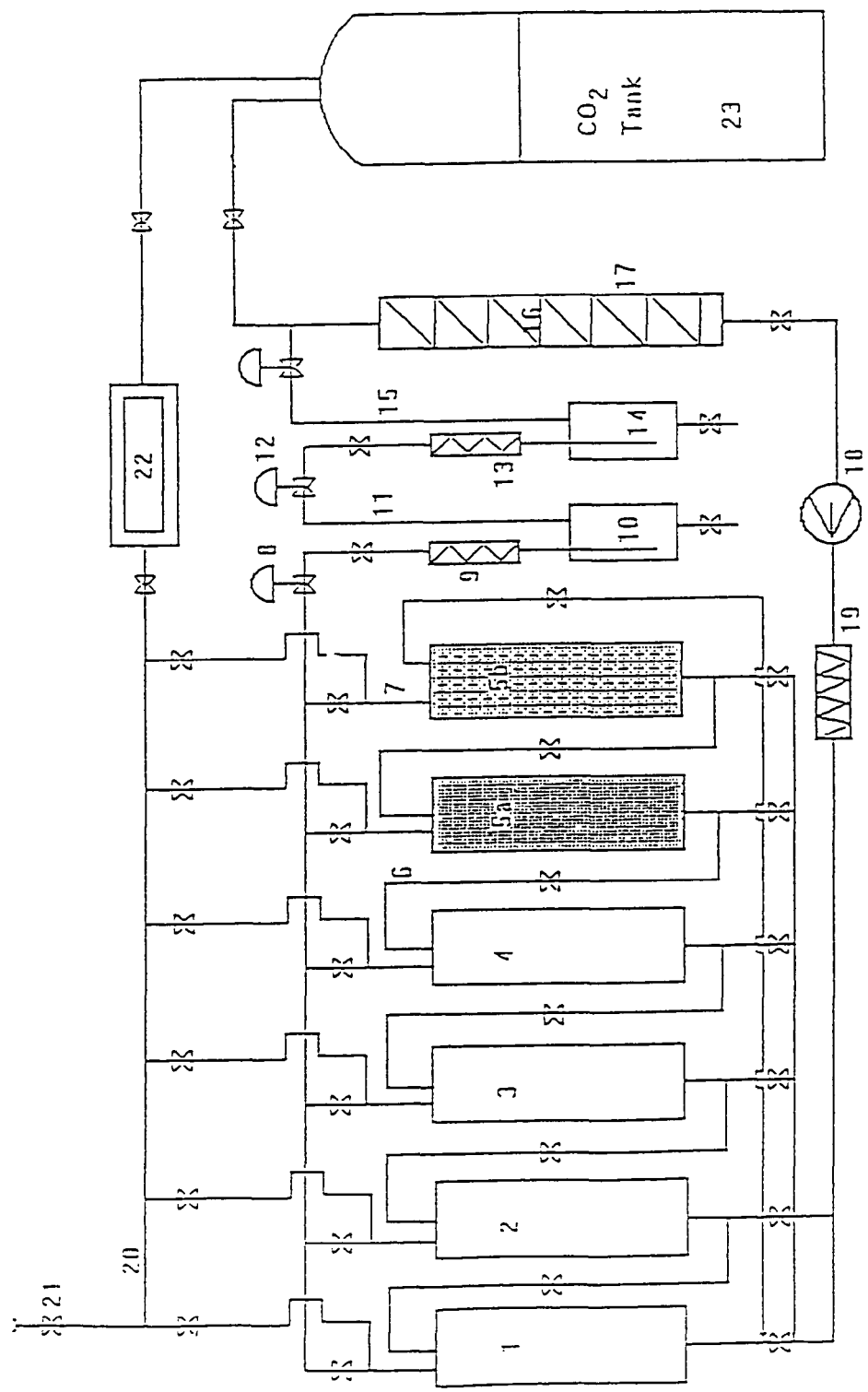
FIG. 1 is a schematic representation of a $CO_2$ extraction plant for producing the primary extract of the invention.

Ground *Cannabis* plant material comprised substantially of inflorescences and leaves is charged into extracting vessels 1-4. $CO_2$ having been brought to a temperature of approx. 60° C. and to a pressure of approx. 250 bar, enters into contact with the material to be extracted in the extracting vessels 1-4 and extracts the desired cannabinoid components, in particular comprising $\Delta^9$-tetrahydrocannabinol and cannabidiol as well as the carboxylic acids thereof. Suitably for extraction a flow rate of 50-150 kg of $CO_2$/kg of starting material is used.

At the upper end of extracting vessel 4, an extract enriched in the cannabinoids leaves the vessel via conduit 6a and arrives at the bottom of separating vessel 5a. The separating vessels 5a and 5b are in the exemplary case filled with various zeolitic molecular sieves and with diatomaceous earth as an adsorbent. In separating vessels 5a and 5b, the same pressure and temperature conditions prevail as in extracting vessels 1-4. The zeolitic molecular sieves placed in container 6a have an internal surface of approx. 800 m²/g, the zeolitic molecular sieves placed in container 6b have an internal surface of approx. 1200 m²/g.

By charging containers 6a and 5b with molecular sieves—preferred, however not indispensable—alkaloids, flavonoids and chlorophylls are further separated from the $CO_2$ loaded with extract. This $CO_2$ extraction mixture thus purified exits from the head of vessel 5b via conduit 7, pressure regulation valve 8, with extraction pressure being reduced to less than 75 bar, in the exemplary case to approx. 60 bar. The $CO_2$ extract mixture then arrives at heat exchanger 9 where it is heated to a temperature supercritical for $CO_2$, preferably to 45° C.

Under these pressure and temperature conditions, extraction of that extract portion takes place in the separating vessel 10 which essentially still contains undesirable monoterpenes and sesquiterpenes. The extract mixture consisting of $CO_2$ and essentially of $\Delta^9$-THC and cannabidiol as well as the carboxylic acids thereof, exits from separating vessel 10 via conduit 11, pressure regulation valve 12, heat exchanger 13, and finally is conveyed into separating vessel 14.

With the aid of pressure regulation valve 12, the separation pressure in container 14 is set to pressure conditions subcricital for $CO_2$, in the exemplary case 50 bar. The separation temperature in vessel 14 is controlled by heat exchanger 13 to a temperature subcricital for $CO_2$, in the exemplary case about 20° C. Under these conditions the pure $CO_2$ is separated from the primary extract enriched in $\Delta^9$-THC and cannabidiol and the carboxylic acids thereof in separating vessel 14.

The pure $CO_2$ is conveyed via conduit 15 to liqufier 17 that is equipped with a condenser coil 16. From here the liquid $CO_2$ is supplied via pressurizing pump 18 to heat exchanger 19, to be available for the following extraction cycle.

For opening the extracting vessel, i.e. for charging and emptying the vessels with, or of, the starting material, the $CO_2$ is either vented directly via conduit 21, or supplied via conduit 20 to recycling plant 22 which then pumps the liquid $CO_2$ into the $CO_2$ storage vessel 23.

Figure 2:
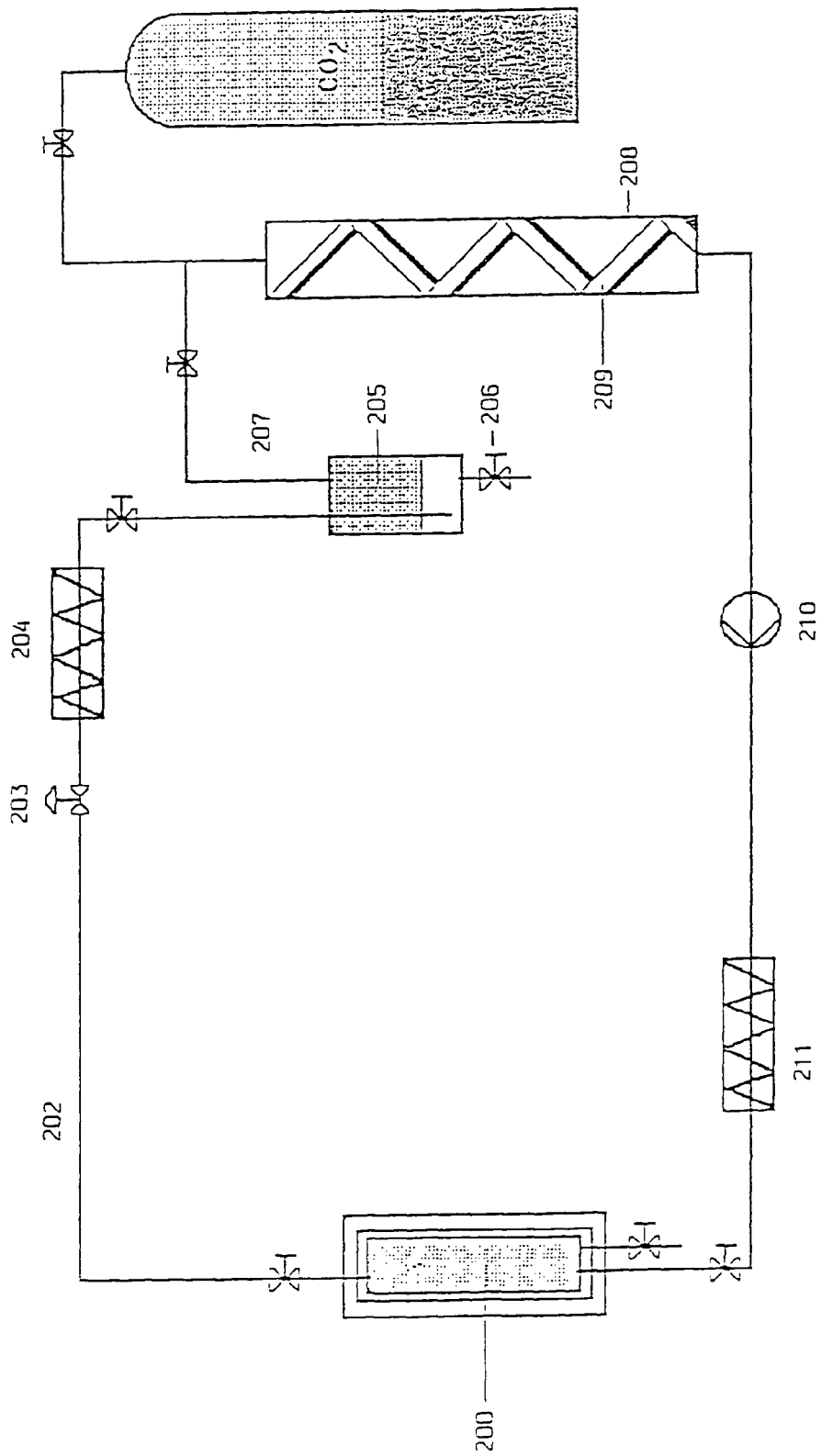
FIG. 2 is a schematic representation of a $CO_2$ extraction plant for producing a secondary extract highly enriched in $\Delta^8$-THC and $\Delta^9$-THC.

FIG. 2 shows a schematic representation of a $CO_2$ extraction plant for producing a secondary extract highly enriched in $\Delta^8$-THC and $\Delta^9$-THC.

For the reaction, in particular the decarboxylation, of the cannabinoid carboxylic acids contained in the primary extract into $\Delta^9$-THC and CBD, the primary extract in the exemplary case is treated during about 2 hours at 80° C.

A mixture of decarboxylated primary extract, water-binding agent and catalyst is introduced into the extracting vessel 200. $CO_2$ at a temperature of 70° C. and a pressure of 300 bar enters into contact with the material to be extracted and extracts the desired components.

Following cyclization, the secondary extract highly enriched in $\Delta^8$-THC and $\Delta^9$-THC exits from vessel 200 at the top end of extracting vessel 200 via conduit 202 and arrives in separating vessel 205 via regulating valve 203—wherein pressure is reduced to 60 bar or 55 bar, respectively—and heat exchanger 204, the temperature being 30° C. or 25° C., respectively. Through valve 206 the secondary extract thus obtained, which contains small amounts of CBD and is highly enriched in $\Delta^8$-THC and $\Delta^9$-THC, may be withdrawn from separating vessel 205.

The pure $CO_2$ is conveyed via conduit 207 to liquefier 208 which is equipped with a condenser coil 209. From there the liquid $CO_2$ is supplied via pressurizing pump 210 to heat exchanger 211, to be available for the following extraction cycle.

Figure 3:
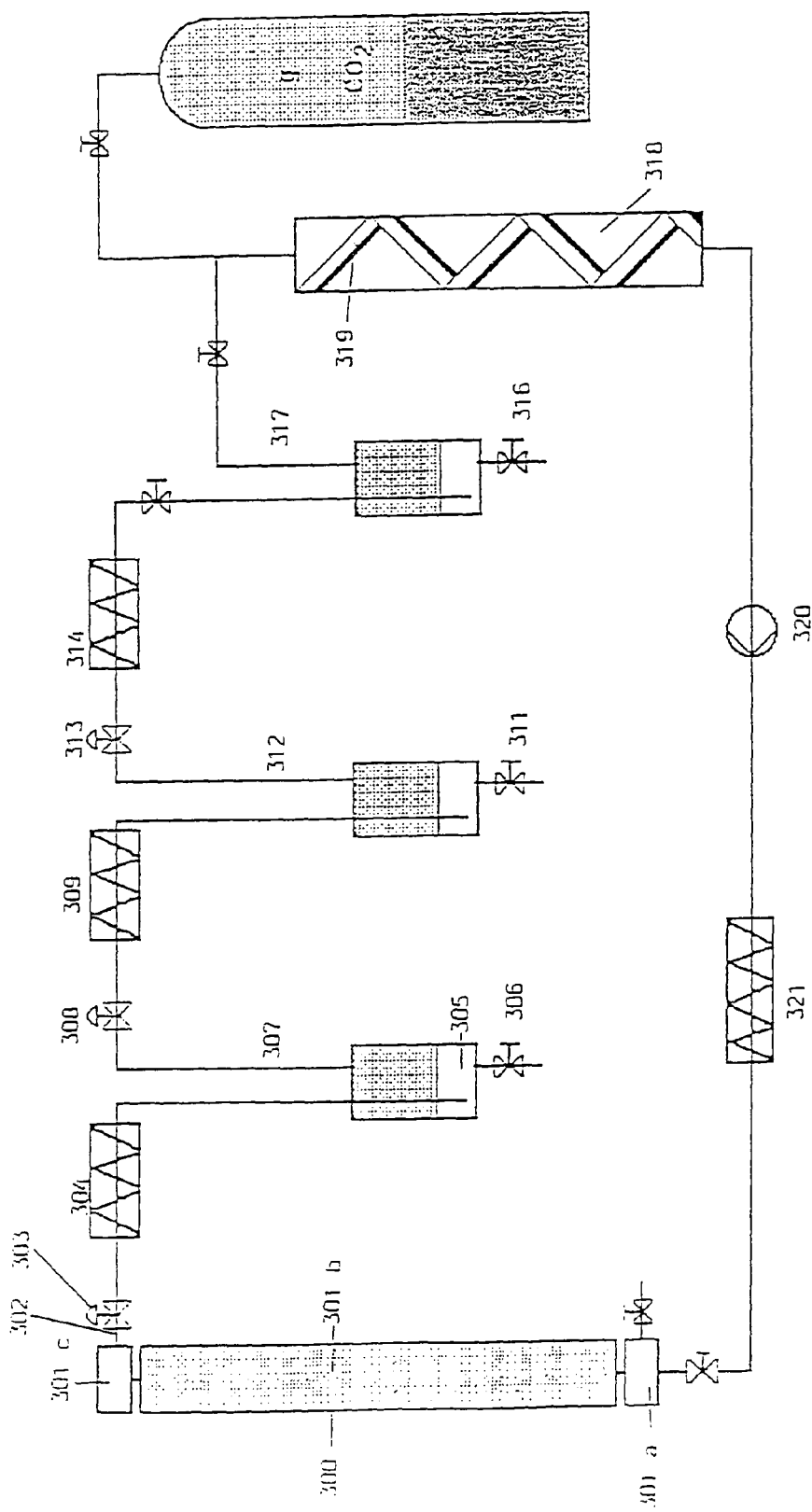
FIG. 3 is a schematic representation of a $CO_2$ extraction plant for separation of a primary and/or secondary extract in CBD, optionally $\Delta^8$-THC and $\Delta^9$-THC in a high-pressure column.

FIG. 3 shows a schematic representation of a $CO_2$ extraction plant for separation of a primary and/or secondary extract CBD, optionally $\Delta^8$-THC and $\Delta^9$-THC, in a high-pressure column.

Via extraction column 300 wherein an extraction pressure of 180 bar and a temperature of 55° C. prevail, consisting of bottom segment 301a, purification segment 301b (charged with silica gel) and head segment 301c, the extract mixture dissolved in $CO_2$ arrives via duct 302, regulating valve 303 and heat exchanger 304 in separating vessel 305, where preferably a pressure of 70 bar and a temperature of 50° C. are to prevail. It is here that the CBD is obtained.

Via duct 307, regulating valve 308 and heat exchanger 309 the extraction mixture arrives in the second separating vessel 310, preferably with a pressure of 60 bar and a temperature of 30° C. prevailing. It is here that the separation of $\Delta^8$-THC takes place. Via valve 311 the obtained $\Delta^8$-THC may be withdrawn.

The $\Delta^9$-THC still dissolved in $CO_2$ is transferred into separating vessel 315 via duct 312, regulating valve 313 and heat exchanger 314. There it is separated out under a pressure of preferably 55 bar and a temperature of preferably 25° C. Via valve 316 the obtained $\Delta^9$-THC may be withdrawn.

The pure $CO_2$ is conveyed via conduit 317 to liquefier 318 which is equipped with a condenser coil 319. From here the liquid $CO_2$ is supplied via pressurizing pump 320 to heat exchanger 321, to be available for the following extraction cycle.

Modifications in the described plant systems are very well possible without the scope of the invention being restricted thereby.

As industrial hemp of the fiber type, in the present exemplary case the French *Cannabis sativa* variety Fedora 19 is employed. The raw drug has an average content of approx. 0.25% of $\Delta^9$-THC and 1.54% of CBD.

As a result, a primary extract having the properties indicated in Table 1 is obtained.

TABLE 1

Primary extracts from industrial hemp with different solvents

| Measured substance | EtOH primary extract | Hexane primary extract* in accordance with WO00/25127 | Inventive primary $CO_2$ extract |
|---|---|---|---|
| Chlorophyll | 3.00% | 2.85% | 0.010% |
| CBD | 14.50% | 12.40% | 58.000% |
| $\Delta^9$-THC | 2.30% | 2.30% | 9.500% |
| $\Delta^8$-THC | 0.00% | 0.00% | 0.000% |
| CBN | 0.50% | 0.50% | 0.100% |
| Flavonoid glycosides | 12.50% | 8.50% | 0.150% |
| Alkaloids: cannabisativin | 0.20% | 0.35% | 0.001% |
| Monoterpenes: | | | |
| α-Pinene | 0.02% | 0.03% | 0.001% |
| β-Pinene | 0.01% | 0.02% | 0.001% |
| Myrcene | 0.02% | 0.02% | 0.001% |
| Sesquiterpenes: | | | |
| Caryophyllene | 0.53% | 0.45% | 0.020% |
| β-Humulene | 0.18% | 0.22% | 0.008% |
| Δ-Selinene | 0.10% | 0.15% | 0.004% |

*This column relates to a test comparing the $CO_2$ extracts in accordance with the present invention with the prior-art hexane extracts of WO00/25127 as discussed at the outset. An industrial hemp having the following raw drug data: water content: 11.2% (wt.); $\Delta^9$-THC 0.25% (wt.); and CBD: 1.54% were extracted with hexane in accordance with WO00/25127. To this end, 100 g of air-dried, pulverized industrial hemp was extracted for 24 hours in 4 l of hexane in accordance with the Soxhlet method. The solvent was removed under reduced pressure, and the obtained extract was analyzed with a view to the parameters indicated in Table 1.

When one compares the data of the $CO_2$ primary extract in accordance with the present invention as shown in Table 1 with the hexane extract in accordance with WO00/25127 and the ethanol extract, initially the relatively good coincidence of the primary extracts obtained by means of the organic solvents is conspicuous.

Moreover in comparison with the $CO_2$ primary extract of the present invention, there results a disadvantageously high chlorophyll content of 3.00% for the hexane extract and of 2.85% for the ethanol extract. For the extract of the invention, the chlorophyll content thus is lower by a factor of almost 300 than in the prior-art extracts.

A low chlorophyll content is particularly advantageous because under certain circumstances, such as when a soft gelatin is used for encapsulation of the extract in the framework of galenic formulation, chlorophyll may involve cross-reticulations which may prevent the active principles contained in the extract from being released.

The desired CBD content is in the inventive $CO_2$ extract higher by a factor 4 to 5, and the $\Delta^9$-THC content also by a factor >4, in comparison with the prior-art solvent extracts.

If one regards the overall cannabinoid content, essentially composed of CBD, $\Delta^9$-THC and CBN, it may be seen that even the inventive primary $CO_2$ extract already is made up at more than two thirds of these constituents, whereas the prior-art extracts only contain an overall cannabinoid content of approx. 15 to 17%.

Moreover what is conspicuous in comparison with the extract of the invention are the highly elevated (more than 80-fold) flavonoid glycoside contents of the ethanol and hexane extracts.

The detected terpene and alkaloid quantities are also strongly elevated in comparison with the extracts according to the invention:

The contents of undesirable monoterpenes listed in Table 1 are higher by a factor of 10-30 than in the two primary extracts obtained with ethanol and hexane than in the $CO_2$ primary extract, and while the sesquiterpene content is higher by a factor 20 to 40 than in the inventive $CO_2$ extracts.

It is moreover noted that the primary extracts obtained with the aid of lipophilic solvents contain the alkaloids that are readily soluble in these solvents, such as, e.g., cannabisativin which is highly cytotoxic. This alkaloid contamination may very well also still occur in an extract prepared in accordance with WO00/25127 from the primary extract described there, following additional purification and enrichment steps in accordance with WO00/25127 which extract is said to have a 98% content of $\Delta^9$-THC.

In contrast, already the primary extracts of the invention without any further purification steps—as shown in Table 1—practically do not contain any more cannabisativin.

Thus the ethanol extract contains about 200 times more toxic alkaloids, in particular the highly cytotoxic cannabisativin, and the hexane extract in accordance with WO00/25127 even about 350 times more than the $CO_2$ primary extract of the invention.

Thus the $CO_2$ extracts of the present invention are superior both to the hexane extracts in accordance with WO00/25127 and to the customary ethanol extracts, because of their high cannabinoid contents and the fact that they are largely free from alkaloids, flavonoid glycosides, mono- and sesquiterpenes.

What is particularly advantageous is the circumstance that the present invention starts out from a hemp having a THC proportion near Zero, which is not even the case in WO00/25127 as this reference starts out from higher THC concentrations in the raw drug inasmuch as drug hemp, not industrial hemp is extracted there.

In view of this very fact it thus is already surprising that THC and cannabinoids may at all be enriched in technically useful amounts from readily available industrial hemp by means of $CO_2$ extraction.

Table 2 shows the components of a secondary extract after completed anellation.

TABLE 2

Secondary extract following cyclization (FIG. 2)

| Measured substance | $CO_2$ secondary extract<br>$P_1 = 300$ bar<br>$T_1 = 70°$ C.<br>$P_2 = 55$ bar<br>$T_2 = 25°$ C. |
|---|---|
| Chlorophyll | 0.01% |
| CBD | 1.5% |
| $\Delta^9$-THC | 41.2% |
| $\Delta^8$-THC | 24.3% |
| CBN | 0.1% |

Table 3 shows the components of a primary extract purified by high-pressure column in accordance with FIG. 3.

TABLE 3

Purified primary extract after chemical purification in a high-pressure column (FIG. 3)

Purified primary extract
$P_1 = 180$ bar
$T_1 = 55°$ C.
$P_2 = 70$ bar (separating vessel No. 5)
$T_2 = 50°$
$P_3 = 60$ bar (separating vessel No. 10)
$T_3 = 30°$ C.
$P_4 = 55$ bar (separating vessel No. 15)
$T_4 = 25°$ C.

| Measured substance | Separator No. 5 | Separator No. 10 | Separator No. 15 |
|---|---|---|---|
| Chlorophyll | 0.01% | 0.01% | 0.01% |
| CBD | 85.0% | 0.0% | 1.5% |
| $\Delta^9$-THC | 2.0% | 0.0% | 87.0% |
| $\Delta^8$-THC | 0.0% | 0.0% | 0.0% |
| CBN | 0.1% | 0.1% | 0.1% |

Table 4 shows the components of a secondary extract which was purified in a high-pressure column.

TABLE 4

Purified secondary extract following purification in a high-pressure column (FIG. 3)

Purified secondary extract
$P_1 = 180$ bar
$T_1 = 55°$ C.
$P_2 = 70$ bar (separating vessel No. 5)
$T_2 = 50°$ C.
$P_3 = 60$ bar (separating vessel No. 10)
$T_3 = 30°$ C.
$P_4 = 55$ bar (separating vessel No. 15)
$T_4 = 25°$ C.

| Measured substance | Separator No. 5 | Separator No. 10 | Separator No. 15 |
|---|---|---|---|
| Chlorophyll | 0.01% | 0.01% | 0.01% |
| CBD | 90.0% | 0.1% | 0.3% |
| $\Delta^9$-THC | 0.5% | 1.0% | 96.0% |
| $\Delta^8$-THC | 0.2% | 85.0% | 1.5% |
| CBN | 0.1% | 0.1% | 0.1% |

It is, of course, fundamentally also possible to use a drug hemp for carrying out the process of the invention.

The above mentioned primary extract is treated further in accordance with the description in FIG. 2 and FIG. 3 and is suited as an active principle for the production of a medicament for the indications described at the outset.

Suitable application types are inhalation, oral, parenteral, as well as enteral application.

In Column 8, Lines 37-45, please delete " 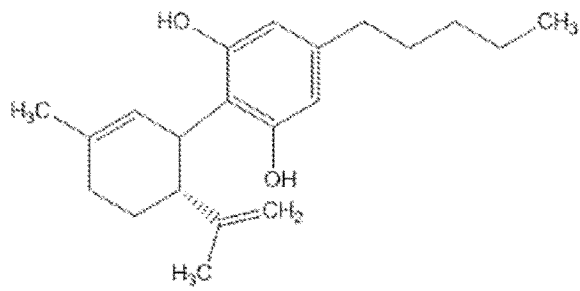 " and insert 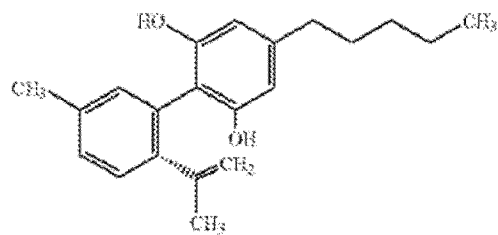 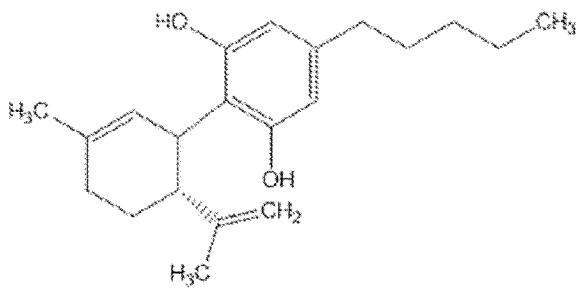

The invention claimed is:

1. A process for producing cannabidiol from a primary extract from industrial hemp plant material containing tetrahydrocannabinol and cannabidiol and optionally the carboxylic acids thereof, wherein said primary extract is obtained by a process comprising
  extracting dried comminuted industrial hemp plant material by means of $CO_2$
  (a) under supercritical pressure and temperature conditions at a temperature in a range of approx. 31° C. to 80° C. and at a pressure in a range of approx 75 bar or 500 bar, or
  (b) in liquefied form in the subcritical range at a temperature of approx. 20° C. to 30° C. and a supercritical pressure of approx. 100 bar to 350 bar; or
  (c) in liquefied form under subcritical pressure and temperature conditions; and
  separating the obtained primary extract out under subcritical conditions or under conditions subcritical in terms of pressure and supercritical in terms of temperature; and
  wherein said primary extract contains reduced proportions of at least monoterpene and sesquiterpene hydrocarbons, alkaloids, flavonoids and chlorophylls; and
  wherein process for producing cannabidiol from a primary extract comprises
  decarboxylating cannabidiolic acid and tetrahydrocannabidiolic acid in said primary extract into cannabidiol and tetrahydrocannabinol through increase in temperature; and
  dissolving the decarboxylated primary extract in the $CO_2$ extracting agent used, and in this condition treating by means of a high-pressure vessel charged with a catalyst for anellation of cannabidiol into tetrahydrocannabinol and a water-binding agent, wherein cannabidiol is reacted to give tetrahydrocannabinol; and
  separating the product enriched in tetrahydrocannabinol at pressure and temperature conditions subcritical for $CO_2$.

2. A process for producing cannabidiol from a primary extract from industrial hemp plant material containing tetrahydrocannabinol and cannabidiol
  and optionally the carboxylic acids thereof, wherein said primary extract is obtained by a process comprising
    extracting dried comminuted industrial hemp plant material by means of $CO_2$
  (a) under supercritical pressure and temperature conditions at a temperature in a range of approx. 31° C. to 80° C. and at a pressure in a range of approx. 75 bar or 500 bar, or
  (b) in the subcritical range at a temperature of approx. 20° C. to 30° C. and a supercritical pressure of approx. 100 bar to 350 bar; or
  (c) under subcritical pressure and temperature conditions; and
    separating the obtained primary extract out under subcritical conditions or under conditions subcritical in terms of pressure and supercritical in terms of temperature; and
    wherein said primary extract contains reduced proportions of at least monoterpene and sesquiterpene hydrocarbons, alkaloids, flavonoids and chlorophylls; and
    wherein process for producing cannabidiol from a primary extract comprises
    decarboxylating cannabidiolic acid and tetrahydrocannabidiolic acid in said primary extract into cannabidiol and tetrahydrocannabinol through increase in temperature; and subsequently separating the cannabidiol through column chromatography on silica gel or preparative high-pressure liquid chromatography.

3. A process for producing an extract containing tetrahydrocannabinol, cannabidiol and optionally the carboxylic acids thereof from dried comminuted industrial hemp plant material, comprising
   (1) subjecting said plant material to a stream of $CO_2$
      (1a) under supercritical pressure and temperature conditions at a temperature in a range of approx. 31° C. to 80° C. and at a pressure in a range of approx. 75 bar or 500 bar, or
      (1b) in liquefied form in the subcritical range at a temperature of approx. 20° C. to 30° C. and a supercritical pressure of approx. 100 bar to 350 bar; or
      (1c) in liquefied found under subcritical pressure and temperature conditions; to extract cannabinoid components;
   (2) reducing the pressure and/or temperature of the extract loaded $CO_2$ in at least two steps, wherein
      (2a) in a first step pressure and/or temperature are reduced whereby monoterpenes and sesquiterpenes are separated from tetrahydrocannabinol and cannabidiol by differential solubility,
      (2b) in a subsequent step pressure is reduced to a pressure subcritical for $CO_2$, whereby tetrahydrocannabinol and cannabidiol are separated from said $CO_2$,
      (2c) subjecting the $CO_2$ extracted from step (2b) to increased pressure and temperature and recycling said $CO_2$ to step (1).

4. The process of claim 3, wherein step (2) further comprises exposure to adsorbent or absorbent to remove alkaloids, flavinoids, and chlorophylls.

* * * * *

UNITED STATES PATENT AND TRADEMARK OFFICE
CERTIFICATE OF CORRECTION

PATENT NO. : 8,895,078 B2
APPLICATION NO. : 10/399362
DATED : November 25, 2014
INVENTOR(S) : Adam Mueller Page 1 of 1

It is certified that error appears in the above-identified patent and that said Letters Patent is hereby corrected as shown below:

In the Claims

At Column 14, Claim number 1, Line number 11, replace the phrase "in a range of approx. 75 bar or 500 bar" with the phrase "in a range of approx. 75 bar to 500 bar".

At Column 14, Claim number 2, Line number 47, replace the phrase "in a range of approx. 75 bar or 500 bar" with the phrase "in a range of approx. 75 bar to 500 bar".

At Column 15, Claim number 3, Line number 11, replace the phrase "in a range of approx. 75 bar or 500 bar" with the phrase "in a range of approx. 75 bar to 500 bar".

Signed and Sealed this
Eleventh Day of June, 2019

Andrei Iancu
*Director of the United States Patent and Trademark Office*

UNITED STATES PATENT AND TRADEMARK OFFICE
CERTIFICATE OF CORRECTION

PATENT NO. : 8,895,078 B2
APPLICATION NO. : 10/399362
DATED : November 25, 2014
INVENTOR(S) : Adam Mueller Page 1 of 3

It is certified that error appears in the above-identified patent and that said Letters Patent is hereby corrected as shown below:

In the Specification

In Column 2, Line 46, please delete "Tetrahydrocannabinol carboxylic acid" and insert --$\Delta^9$-Tetrahydrocannabinol--

In Column 2, Line 57, please delete "$\Delta^9$-Tetrahydrocannabinol $\Delta^9$-" and insert --$\Delta^9$-Tetrahydrocannabinol carboxylic acid--

In Column 3, Lines 12-20, please delete " 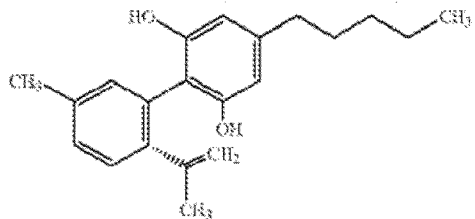 " and insert

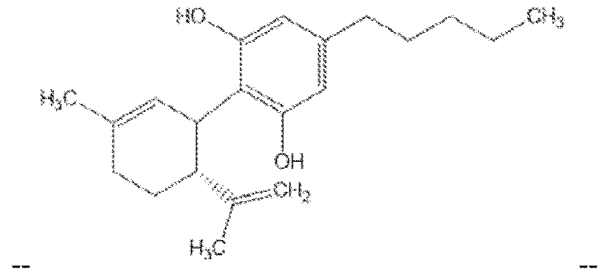

-- --

Signed and Sealed this
Twenty-seventh Day of October, 2020

Andrei Iancu
*Director of the United States Patent and Trademark Office*

In Column 3, Lines 22-30, please delete " 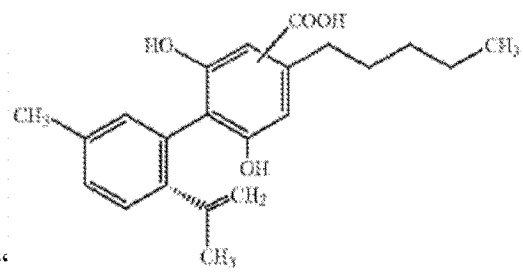 " and insert

-- 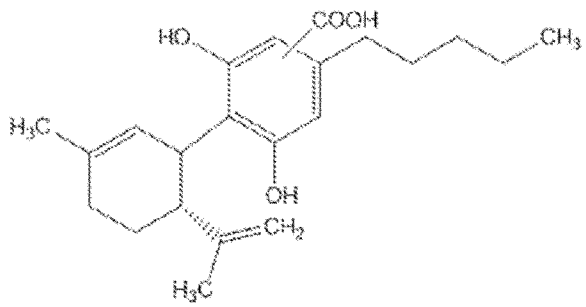 --

In Column 7, Lines 47-49, please delete "Δ$^8$-THC is an isomer of Δ$^9$-THC and forms substantially during the cyclization of CBD zu Δ$^9$-THC as well as in the presence of acids." and insert --Δ$^8$-THC is an isomer of Δ$^9$-THC and forms substantially during the cyclization of CBD to Δ$^9$-THC as well as in the presence of acids.--

In Column 7, Lines 55-64, please delete " 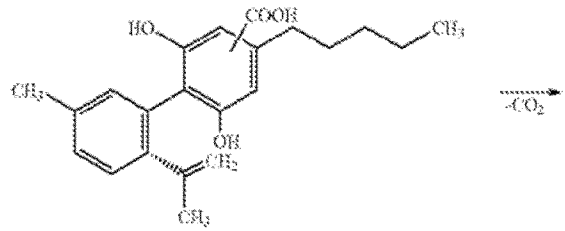 " and insert

-- 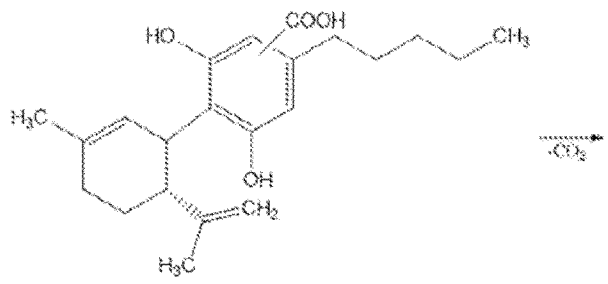 --

In Column 8, Lines 1-10, please delete " 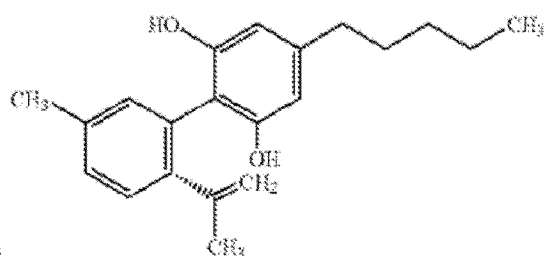 " and insert

CERTIFICATE OF CORRECTION (continued)
U.S. Pat. No. 8,895,078 B2